United States Patent [19]

Saleh et al.

[11] Patent Number: 5,239,569
[45] Date of Patent: Aug. 24, 1993

[54] RADIOGRAPHIC ANALYSIS OF BONES

[76] Inventors: Michael Saleh, 176A Stannington View Road, Crookes, Sheffield, South Yorkshire S10 1ST; Stephen P. Harriman, 25 Old Hay Close, Dore, Sheffield, South Yorkshire S17 3GP, both of United Kingdom

[21] Appl. No.: 753,740

[22] Filed: Sep. 3, 1991

Related U.S. Application Data

[63] Continuation-in-part of Ser. No. 492,533, Mar. 12, 1990, abandoned.

[30] Foreign Application Priority Data

Mar. 10, 1989 [DE] Fed. Rep. of Germany ... 8903054[U]
Sep. 20, 1989 [GB] United Kingdom ................. 8921300

[51] Int. Cl.$^5$ .............................................. H05G 1/28
[52] U.S. Cl. .................................... 378/163; 378/164; 378/207
[58] Field of Search ................. 378/163, 164, 205, 170

[56] References Cited

U.S. PATENT DOCUMENTS

| | | | |
|---|---|---|---|
| 2,276,137 | 3/1942 | Young | 378/164 |
| 2,344,823 | 3/1944 | Landis et al. | 378/164 |
| 3,171,959 | 3/1965 | Kozek et al. | 378/164 |
| 4,187,423 | 2/1978 | Ehrhardt | 378/164 |
| 4,918,715 | 4/1990 | Krupnick et al. | 378/164 |

*Primary Examiner*—Janice A. Howell
*Assistant Examiner*—Don Wong
*Attorney, Agent, or Firm*—McAndrews, Held & Malloy, Ltd.

[57] ABSTRACT

A hand portable aid for use in the real time radiographic analysis of bones and comprising a substantially rigid sheet of x-ray pervious material at least as large as the bone and carrying a radio-opaque marker against which alignment of the bone may be checked.

14 Claims, 1 Drawing Sheet

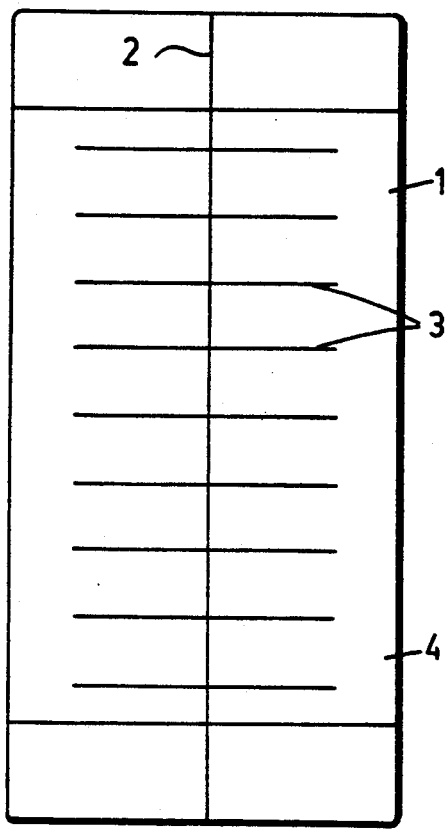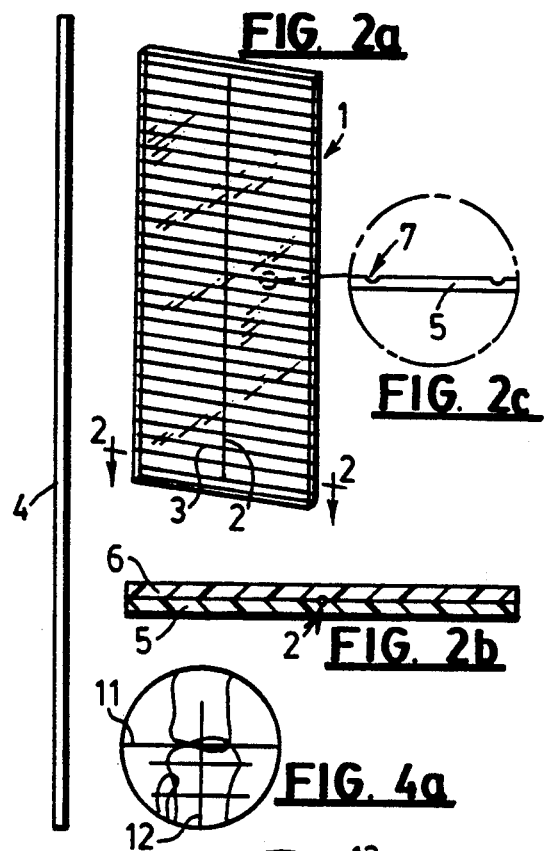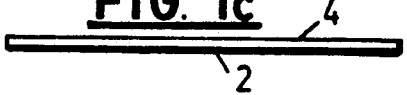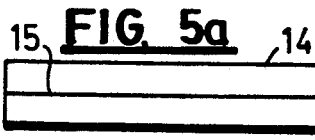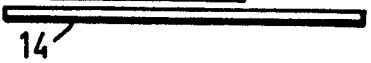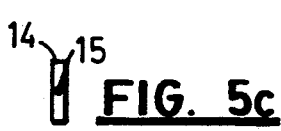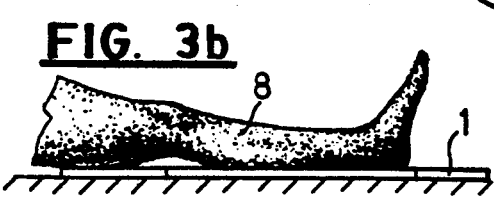

RADIOGRAPHIC ANALYSIS OF BONES

BACKGROUND OF THE INVENTION

This invention is a continuation in part of co-pending U.S. application Ser. No. 07/492,533 for "Improvements in the Radiographic Analysis of Bones" filed Mar. 12, 1990 now abandoned. U.S. application Ser. No. 07/492,533 was filed claiming a priority date under 35 U.S.C. §119 for West German utility model application G8903054.0 of Mar. 10, 1989 and U.K. Pat. application 8921300.3 of Sep. 20, 1989.

FIELD OF THE INVENTION

This invention relates to an aid for use in radiographic analysis of bones and particularly to a device used to aid the reduction of a bone fracture or produce a precise change in alignment in a surgically divided bone. The aid is particularly useful during procedures in an operating theatre but may also be used in an outpatient department.

Bone fractures are currently reduced by eye and the overall bony alignment confirmed by radiographic analysis using a conventional radiograph. This results in the necessity of breaching the sterile field in order to place the radiographic cassette in the correct position and to retrieve it after the exposure has been made. The whole procedure may take upwards of 10 minutes and may require repeating if the correct alignment of the bone has not been obtained. If the alignment is not correct the bone must be reset with consequent distress to the patient and an increase in the use of hospital resources.

It is extremely important to achieve good bone alignment not only to ensure that the broken bone is straight but also to ensure that the axes of joints at the ends of the bone are aligned. For example, in the case of a leg broken between the knee and the ankle, it is essential to ensure that the axis of the knee joint is parallel to the axis of the ankle joint, for otherwise the patient will have difficulty in walking properly. It may also be necessary to ensure that the joint centers are on the principal bone axis or are offset by a predetermined amount from that axis.

Currently mobile x-ray image intensification units use a coupled television system to visualize the bone in real time, but the field of view is not large enough to view the whole of the bone and so get an impression of the alignment. Typically an image of about six inches in diameter is obtained and this is not sufficiently large to obtain an accurate assessment of the overall alignment. Also there is some distortion of the image at the edge of the field of view which further hampers assessment of bone alignment.

The invention is an aid to be used in real time conjunction with an image intensification unit and is especially useful in the setting of long bone fractures and in corrective surgery of the long bones such as the humerus, radius, and ulna, femur and tibia and fibula.

In order to check alignment it is necessary to move the image intensification unit from one end of the bone to the other but, in the absence of a suitable guide it is difficult to check the alignment of the bone.

PRIOR ART OF THE INVENTION

Devices have been proposed for use in x-ray photography in which features of the human anatomy are photographed against a grid of x-ray opaque material. The grid is inserted between the x-ray source and film, and the resulting exposure shows a shadow of the tissue against a dimensionally accurate grid. Such photographs are used for comparative reference, and diagnostic purposes. These devices have not, however, been proposed for use in real time fluoroscopy where the alignment of the bone is checked in real time against a guide.

U.S. Pat. No. 2,344,824—Landis et al. discloses a fine marking grid for use with an x-ray photographic plate and intended for use in a method of detecting misalignment of bone structure. The disclosed method permits a comparison of normally symmetrical parts of a human bone structure.

U.S. Pat. No. 4,918,715—Krupnick et al. discloses a flexible substrate having an x-ray opaque grid and for use in marking the exterior of a patient's body prior to invasive surgery. The substrate deforms to closely match the body contours and is removed prior to surgery.

U.S. Pat. No. 3,171,959—Kozek et al. discloses a marking grid having a plurality of spaced x-ray opaque parallel lines for providing measurements and for use with an x-ray photographic device.

A particular feature of prior art measuring devices is that none are suitable for use in real time in extending the field of view of mobile x-ray image intensification unit.

Furthermore none of the prior art devices known to the applicants is for use in procedures performed in operating theatres, and none are specifically for orthopedic or bone fracture applications.

SUMMARY OF THE INVENTION

According to the invention there is provided a hand portable aid for use in the real time radiographic analysis of bones, the aid comprising a substantially rigid sheet of x-ray pervious material at least as large as the bone or bones to be analyzed and carrying a radio-opaque marker or other x-ray attenuating material against which alignment of the bone may be checked. Preferably the sheet is of carbon fiber, polycarbonate or polymethyl methacrylate (PERSPEX) or other low attenuating material, and the marker is in the form of several mutually perpendicular lines of high attenuating material.

It is essential that the aid be substantially rigid for otherwise it could not provide a reference for checking alignment. The flexible sheet of Krupnick et al. is wholly unsuitable. The aid must be sufficiently rigid to resist deformation as the patient is moved about on the operating table.

Whilst it is essential that the aid is at least as large as the bone or bones to be analyzed. It is important that the aid is not so large that it cannot be manipulated by hand into approximately the correct position.

In a preferred embodiment the marker comprises a grid of discrete lead wires or of similar material having a high atomic number. The radio-opaque marker is preferably incorporated within the sheet for protection and to give a device which is easily cleaned and sterilized.

In one preferred embodiment the aid is approximately 600 mm by 300 mm and approximately 4–5 mm thick. Lead wires of approximately 1 mm thickness are preferred.

Since the aid is for use in real time surgery and thus within the sterile field, it is essential that it be capable of sterilization by normal techniques and is preferably sufficiently robust to be capable of repeated sterilization.

The invention also provides a method of using the aid in preparation of a bone or bones for surgery or treatment, the method comprising the steps of placing the bone or bones over the aid, providing a real time x-ray image of the bone or bones against the aid and comparing the relative position of bone or bones and marker.

In a preferred embodiment the aid includes a radio-opaque grid and, when used for bone alignment, the method further includes the step of adjusting the position of the aid until the aid is approximately aligned with the bone and adjusting the position of the bone until the image of the bone adopts a desired alignment with the grid. The bone may then be set using any conventional technique, such as plaster, plate and screws, intra medullary nail or external fixator.

In addition to being used in alignment of bone fractures, the device may be used in conjunction with a radio-opaque rule for accurate measurement of bone length; as a means of obtaining an accurate comparison between a pair of bones, and in conjunction with a radio-opaque protractor as a means of designing osteotomies. Two identical aids according to the invention may be used one above and one below the bone to ensure perpendicularity of the x-ray beam with respect to a particular plane through the bone. Alternatively perpendicularity may be checked by the use of two spaced sets of wires in a single perspex sheet to be used either above or below the bone.

In another aspect the aid may be used to check or fix the alignment of the joints at the ends of a bone. In particular both the bone and the axes of respective joints may be aligned with the grid.

BRIEF DESCRIPTION OF THE DRAWING

Other features of the invention will be apparent from the following description of a preferred embodiment shown by way of example only with reference to the accompanying drawings which:

FIG. 1a is a plan view of a preferred embodiment of the device;

FIG. 1b is an elevation of FIG. 1a;

FIG. 1c is an end view of FIG. 1a.

FIG. 2a is a perspective view of an alternative form of the device;

FIG. 2b is a transverse section through FIG. 2a line 2—2;

FIG. 2c is an enlarged view of sheet substrate 5 without the existance of wire 3.

FIG. 3a is a plan view of the aid in use;

FIG. 3b is an elevation of the aid in use.

FIG. 4a is an image of a knee joint and the aid;

FIG. 4b is an image of an ankle joint in one orientation and the aid;

FIG. 4c is an image of an ankle joint in another orientation and the aid.

FIG. 5a is a plan view of a rule for use with the aid of FIGS. 1 and 2.;

FIG. 5b is an elevation of the rule of FIG. 5a;

FIG. 5c is an end view of the rule of FIG. 5a.

FIG. 6 is an image of a bone showing also the aid of the invention and the rule of FIGS. 5a-c.

DETAILED DESCRIPTION OF THE PREFERRED EMBODIMENT

With reference to FIG. 1a-c of the drawings there is shown a device 1 comprising a grid of lead wires 2,3 contained within a clear substrate 4 such as polycarbonate or polymethyl methacrylate.

In the embodiment of FIG. 2, the grid comprises a number of wires 2,3 of round section housed within recesses between two sheets of substrate 5,6; the wires stop short of the edges of the sheets 5,6 as shown. The wires may be laid in slots milled in the surface of the substrate and sealed therein. The sheets 5,6 are sealed to each other so that the aid may be readily cleaned and sterilized after use without the risk of damaging the grid.

Since the device is used in surgery and thus within the sterile field it is most important that it be suitable for sterilizing in an autoclave.

The grid may be formed of strips of lead or of any other suitable radio-opaque material which provides sufficiently dense and dark lines. Marks, such as the notches 7 may be provided as an alternative to additional longitudinal threads which would increase the manufacturing cost and might obscure the bone image in use.

The number and extent of transverse wires may be chosen to suit the size and type of bone being set. A number of such devices with differing grid configurations may be made available for use. In the example of FIG. 1a the aid measures 600×300×4 mm with the longitudinal wire and outer transverse wires extending to the periphery of the aid. The outer transverse wires are 70 mm from the respective ends and the intermediate wires are 50 mm apart and symmetrical about the center line as shown. The intermediate wires may be closer if desired, for example 25 mm apart.

The outer transverse wires define reference lines between which should lie the bone or bones to be imaged; these reference lines should preferably extend across the full width of the aid. The intermediate wires are in the preferred embodiment about 22 mm long, but should in any event be sufficiently long to extend the full diameter of the real time T.V. image.

Longer and wider grids may be used for determination of the mechanical axis of the limb and to perform comparisons between a pair of limbs.

A narrow perspex strip containing one longitudinal wire or a set comprising a calibrated protractor of radio-opaque material may be placed on the aid to position and design osteotomies as will be further described below.

Use of the aid is now described with reference to a broken leg. The aid 1 is placed below the leg 8 and aligned approximately with the broken bone as illustrated in FIGS. 3a and 3b.

The image intensification is used to image the knee joint, as illustrated in FIG. 4a, and nearest reference line 11 on the aid is moved, under fluoroscopy, so that it passes through the center of the knee joint.

The image intensification is tracked linearly down the leg and may be used to check the fracture site in passing. The ankle joint is then imaged as illustrated in FIG. 4b. In a normal leg the axis of the knee joint is parallel to the axis of the ankle joint, but in a broken leg the ankle axis may not be aligned with the transverse grid wires— FIG. 4b illustrates such a situation, the ankle axis being shown approximately by dotted line 13.

To correct alignment, the ankle joint is manipulated, as illustrated in FIG. 4c, until the joint axis 13 is parallel to the transverse grid lines and thus parallel to the knee joint axis. The grid center line should pass through the ankle center line thus conforming that the ankle joint has been restored to its original relative position. The broken bone may then be set using any desired method.

In some cases the joint center lines may not coincide in which case the aid may be used to determine the offset of a symmetrical bone, and thereafter be used to set the corresponding broken bone with the same offset. In the case described above the unbroken leg may be used to provide a reference prior to using the aid in setting the broken leg.

FIGS. 5a–c illustrate a radio-opaque rule 14 used in osteotomies. The rule comprises a flat strip of material containing a radio-opaque line 15 and may be made in the same manner as the aid described above. The rule may typically be 300 mm × 25 mm × 4 mm and contain a lead wire of 1 mm in diameter.

FIG. 6 illustrates use of the rule in designing an osteotomy where a bone is to be cut in a precise and predetermined manner. The rule 14 is represented by the dotted outline and may be secured to the aid 1 in any suitable fashion to form a precise angle. The surgeon can thus cut a precise wedge of bone along lines defined by the rule and the aid and as seen on the T.V. image.

What is claimed is:

1. A hand portable aid for use in the real time radiographic analysis of bones and comprising a substantially rigid sheet of x-ray pervious material at least as large as the bone and carrying a radio-opaque marker sealed within the sheet against which marker alignment of the bone is checked in use wherein the marker further comprises a longitudinal wire and a plurality of transverse wires extending on either side of said longitudinal wire.

2. A hand portable aid for use in the real time radiographic analysis of bone comprising a substantially rigid sheet of x-ray pervious material at least as large as the bone and carrying a grid of radio-opaque markers including a longitudinal wire, a plurality of transverse reference wires symmetrically extending a grid width distance from the longitudial wire and a plurality of intermediate reference wires extending symmetrically a distance less than the grid width distance from the longitudinal wire and positioned intermediate the reference wires.

3. An aid according to claim 2 wherein the marker comprises a grid of discrete lead wires.

4. An aid according to claim 3 wherein the grid is sealed within the sheet.

5. An aid according to claim 4 wherein the sheet is transparent.

6. An aid according to claim 5 wherein the sheet is of polycarbonate.

7. An aid according to claim 5 wherein the sheet is of polymethyl methacrylate.

8. An aid according to claim 7 wherein said sheet comprises two layers of polymerized methyl methacrylate having said marker sandwiched therebetween.

9. A hand portable aid for use in real time radiographic analysis of bones and comprising a substantially rigid sheet of x-ray pervious material at least as large as the bone to be analyzed, said sheet carrying a radiographic analysis marker against which marker alignment of the bone is checked, in use said marker comprising a first radio-opaque line at least as long as the bone to be analyzed, and a plurality of spaced second radio-opaque lines perpendicular to said first line.

10. An aid according to claim 9 wherein said plurality of second radio-opaque lines includes two spaced reference lines symmetrical about said first line, and a plurality of equispaced lines intermediate said reference lines, symmetrical about said first line and shorter than said reference lines.

11. An aid according to claim 9 and further including rule comprising a narrow strip of x-ray pervious material having a single straight radio-opaque marker extending longitudinally therethrough, said rule being shorter than the width of said aid.

12. A method of using a hand portable aid for use in real time radiographic analysis of bones in preparation of a bone for surgery or treatment, said aid having a substantially rigid sheet of x-ray pervious material at least as large as a bone to be analyzed, said sheet carrying a radiographic analysis marker against which marker alignment of the bone is checked in use, said marker including a first radio-opaque line at least as long as the bone to be analyzed and a plurality of spaced second radio-opaque lines perpendicular to said first line, and method comprising the steps of:
   placing the bone against said aid;
   providing an x-ray image of the bone against said aid; and
   comparing the relative position of bone and marker.

13. A method according to claim 12 and including the fourth step of:
   adjusting the position of said bone until the image adopts a desired alignment.

14. A method according to claim 13 and including the fifth step of adjusting the position of the joints of said bone until the respective joint axes adopt a desired alignment.

* * * * *